US008249705B1

(12) United States Patent
Kieval et al.

(10) Patent No.: US 8,249,705 B1
(45) Date of Patent: Aug. 21, 2012

(54) DEVICES, SYSTEMS, AND METHODS FOR IMPROVING LEFT VENTRICULAR STRUCTURE AND FUNCTION USING BAROREFLEX ACTIVATION THERAPY

(75) Inventors: Robert S. Kieval, Medina, MN (US); Martin Rossing, Coon Rapids, MN (US)

(73) Assignee: CVRx, Inc., Minneapolis, MN (US)

( * ) Notice: Subject to any disclaimer, the term of this patent is extended or adjusted under 35 U.S.C. 154(b) by 635 days.

(21) Appl. No.: 12/043,754

(22) Filed: Mar. 6, 2008

Related U.S. Application Data

(60) Provisional application No. 60/895,913, filed on Mar. 20, 2007.

(51) Int. Cl.
*A61N 1/362* (2006.01)

(52) U.S. Cl. ........... 607/14; 607/1; 607/2; 607/3; 607/9; 607/115; 607/118

(58) Field of Classification Search .................. 607/1–3, 607/9, 14, 115, 118
See application file for complete search history.

(56) References Cited

U.S. PATENT DOCUMENTS

| | | | |
|---|---|---|---|
| 3,645,267 A | 2/1972 | Hagfors | |
| 3,650,277 A | 3/1972 | Sjostrand et al. | |
| 4,014,318 A | 3/1977 | Dockum et al. | |
| RE30,366 E | 8/1980 | Rasor et al. | |
| 4,256,094 A | 3/1981 | Kapp et al. | |
| 4,331,157 A | 5/1982 | Keller, Jr. et al. | |
| 4,481,953 A | 11/1984 | Gold et al. | |
| 4,525,074 A | 6/1985 | Murakami | |
| 4,531,943 A | 7/1985 | Van Tassel et al. | |
| 4,551,862 A | 11/1985 | Haber | |
| 4,586,501 A | 5/1986 | Claracq | |
| 4,640,286 A | 2/1987 | Thomson | |
| 4,641,664 A | 2/1987 | Botvidsson | |
| 4,664,120 A | 5/1987 | Hess | |
| 4,682,583 A | 7/1987 | Burton et al. | |
| 4,702,254 A | 10/1987 | Zabara | |
| 4,709,690 A | 12/1987 | Haber | |
| 4,739,762 A | 4/1988 | Palmaz | |
| 4,762,130 A | 8/1988 | Fogarty et al. | |

(Continued)

FOREIGN PATENT DOCUMENTS
WO  WO-97/18856 A1  5/1997
(Continued)

OTHER PUBLICATIONS

Bilgutay, A.M. et al. (May 1996). "Surgical Treatment of Hypertension with Reference to Baropacing," *The Amer. Jour. of Cardiology* 17:663-667.

(Continued)

*Primary Examiner* — Carl H Layno
*Assistant Examiner* — Deborah Malamud
(74) *Attorney, Agent, or Firm* — Morrison & Foerster LLP

(57) ABSTRACT

Described here are devices, systems, and methods for improving left ventricular function in a patient with systolic heart failure with left ventricular dysfunction using baroreflex activation therapy. In general the systems have at least one electrode and a control system in communication with the electrode, the control system including a processor and memory, wherein the memory includes software defining a stimulus regime configured to effect improvement in left ventricular function. The methods for improving left ventricular function in a subject typically include identifying a patient in need of left ventricular function improvement and stimulating a baroreceptor with a baroreceptor activation device to improve left ventricular function.

15 Claims, 7 Drawing Sheets

U.S. PATENT DOCUMENTS

| | | |
|---|---|---|
| 4,762,820 A | 8/1988 | Gavras |
| 4,770,177 A | 9/1988 | Schroeppel |
| 4,791,931 A | 12/1988 | Slate |
| 4,800,882 A | 1/1989 | Gianturco |
| 4,803,988 A | 2/1989 | Thomson |
| 4,813,418 A | 3/1989 | Harris |
| 4,825,871 A | 5/1989 | Cansell |
| 4,828,544 A | 5/1989 | Lane et al. |
| 4,830,003 A | 5/1989 | Wolff et al. |
| 4,860,751 A | 8/1989 | Callaghan |
| 4,867,164 A | 9/1989 | Zabara |
| 4,881,939 A | 11/1989 | Newman |
| 4,886,062 A | 12/1989 | Wiktor |
| 4,887,608 A | 12/1989 | Mohl et al. |
| 4,917,092 A | 4/1990 | Todd et al. |
| 4,960,133 A | 10/1990 | Hewson |
| 4,969,458 A | 11/1990 | Wiktor |
| 5,025,807 A | 6/1991 | Zabara |
| 5,078,736 A | 1/1992 | Behl |
| 5,113,869 A | 5/1992 | Nappholz et al. |
| 5,117,826 A | 6/1992 | Bartlet et al. |
| 5,170,802 A | 12/1992 | Mehra |
| 5,181,911 A | 1/1993 | Shturman |
| 5,199,428 A | 4/1993 | Obel et al. |
| 5,222,971 A | 6/1993 | Willard et al. |
| 5,224,491 A | 7/1993 | Mehra |
| 5,259,394 A | 11/1993 | Bens |
| 5,295,959 A | 3/1994 | Gurbel et al. |
| 5,299,569 A | 4/1994 | Wernicke et al. |
| 5,304,206 A | 4/1994 | Baker, Jr. et al. |
| 5,314,453 A | 5/1994 | Jeutter |
| 5,318,592 A | 6/1994 | Schaldach |
| 5,330,507 A | 7/1994 | Schwartz |
| 5,330,515 A | 7/1994 | Rutecki et al. |
| 5,458,626 A | 10/1995 | Krause |
| 5,509,888 A | 4/1996 | Miller |
| 5,522,854 A | 6/1996 | Ideker et al. |
| 5,529,067 A | 6/1996 | Larsen et al. |
| 5,531,779 A | 7/1996 | Dahl et al. |
| 5,535,752 A | 7/1996 | Halperin et al. |
| 5,540,734 A | 7/1996 | Zabara |
| 5,545,132 A | 8/1996 | Fagan et al. |
| 5,575,809 A | 11/1996 | Sasaki |
| 5,578,061 A | 11/1996 | Stroetmann et al. |
| 5,634,878 A | 6/1997 | Grundei et al. |
| 5,651,378 A | 7/1997 | Matheny et al. |
| 5,690,681 A | 11/1997 | Geddes et al. |
| 5,692,882 A | 12/1997 | Bozeman, Jr. et al. |
| 5,695,468 A | 12/1997 | Lafontaine et al. |
| 5,700,282 A | 12/1997 | Zabara |
| 5,707,400 A | 1/1998 | Terry, Jr. et al. |
| 5,715,837 A | 2/1998 | Chen |
| 5,725,471 A | 3/1998 | Davey et al. |
| 5,725,563 A | 3/1998 | Klotz |
| 5,727,558 A | 3/1998 | Hakki et al. |
| 5,741,316 A | 4/1998 | Chen et al. |
| 5,800,464 A | 9/1998 | Kieval |
| 5,807,258 A | 9/1998 | Cimochowski et al. |
| 5,814,079 A | 9/1998 | Kieval |
| 5,824,021 A | 10/1998 | Rise |
| 5,876,422 A | 3/1999 | van Groeningen |
| 5,891,181 A | 4/1999 | Zhu |
| 5,913,876 A | 6/1999 | Taylor et al. |
| 5,916,239 A | 6/1999 | Geddes et al. |
| 5,928,272 A | 7/1999 | Adkins et al. |
| 5,967,986 A | 10/1999 | Cimochowski et al. |
| 5,967,989 A | 10/1999 | Cimochowski et al. |
| 5,987,352 A | 11/1999 | Klein et al. |
| 6,006,134 A | 12/1999 | Hill et al. |
| 6,023,642 A | 2/2000 | Shealy et al. |
| 6,050,952 A | 4/2000 | Hakki et al. |
| 6,052,623 A | 4/2000 | Fenner et al. |
| 6,058,331 A | 5/2000 | King |
| 6,061,596 A | 5/2000 | Richmond et al. |
| 6,073,048 A | 6/2000 | Kieval et al. |
| 6,077,227 A | 6/2000 | Miesel et al. |
| 6,077,298 A | 6/2000 | Tu et al. |
| 6,161,029 A | 12/2000 | Spreigl et al. |
| 6,178,349 B1 | 1/2001 | Kieval |
| 6,178,379 B1 | 1/2001 | Dwyer |
| 6,231,516 B1 | 5/2001 | Keilman et al. |
| 6,292,695 B1 | 9/2001 | Webster, Jr. et al. |
| 6,522,926 B1 | 2/2003 | Kieval et al. |
| RE38,705 E | 2/2005 | Hill et al. |
| 2001/0020177 A1 | 9/2001 | Gruzdowich et al. |
| 2004/0106954 A1* | 6/2004 | Whitehurst et al. ............... 607/3 |
| 2004/0254616 A1 | 12/2004 | Rossing et al. |
| 2005/0251212 A1 | 11/2005 | Kieval et al. |
| 2008/0119898 A1 | 5/2008 | Ben-David et al. |

FOREIGN PATENT DOCUMENTS

| | | |
|---|---|---|
| WO | WO-99/26530 A1 | 6/1999 |
| WO | WO-99/42039 A1 | 8/1999 |
| WO | WO-99/42176 A1 | 8/1999 |

OTHER PUBLICATIONS

Bilgutay, A.M. et al. (Nov. 1965). "Baropacing. A New Concept in the Treatment of Hypertension," *Baroreceptors and Hypertension Proceedings of an International Symposium*, Proceedings of the International Symposium, Dayton, Ohio, Nov. 16-17, 1965, p. 425-437.

Böck, P. et al. (1976). "Fine Structure of Baroreceptor Terminals in the Carotid Sinus of Guinea Pigs & Mice," *Cell & Tissue Research* 170:95-112.

Eckberg, D.L. et al. (1992). "Baroreflex Anatomy," Chapter 3 in *Human Baroreflexes in Health & Disease*, Oxford University Press: New York, pp. 19-30.

Frank, G. et al. (Oct. 1967). "Simultaneous Multiple Site Venticular Stimulation," *Circulation*, Supplement No. Two, American Heart Associate Abstracts, XXXVI(4):II-253.

Goldberger, J.J. et al. (Sep. 15, 1999). "New Technique for Vagal Nerve Stimulation," *Journal of Neuroscience Methods* 91(1-2)109-114.

Hainsworth, R. (1995). "Cardiovascular Reflexes From Ventricular & Coronary Receptors," Chapter 15 in *Control o the Cardiovascular and Respiratory Systems in Health and Disease*, Kaooagoda, C,T, et al. eds., Plenum Press: New York, NY, pp. 157-174.

Harrison, D.C. (Mar. 1970). "Carotid Sinus Stimulation for the Treatment of Angina Pectoris," *California Medicine The Western Journal of Medicine* 112(3):78-79.

Itoh, K. (Mar. 1972). "Studies on the Carotid Body & the Carotid Sinus Effects on the Heart by Electrical Stimulation of the Carotid Sinus Wall," *Jap. Heart J.* 13(2)136-149.

Krauhs, J.M. (Feb. 1979). "Structure of Rat Aortic Baroreceptors & Their Relationship to Connective Tissue," *Journal of Neurocytology* 8(1):401-414.

Linblad, L.E. et al. (Mar. 1981). "Circulatory Effects of Carotid Sinus Stimulation & Changes in Blood Volume Distribution in Hypertensive Man," *Acta. Physiol. Scand*. 111:299-306.

Neufeld, H.N. et al. (Jul. 1965). "Stimulation of the Carotid Baroreceptors Using a Radio-Frequency Method," *Israel J. Med. Sci*. 1(4): 630-632.

Reich, T. (Dec. 1969). "Implantation of a Carotid Sinus Nerve Stimulator," *AORN Journal* pp. 53-56.

Schauerte, P. et al. (Jan. 2000). "Transvenous Parasympathetic Nerve Stimulation in the Inferior Vena Cava and Atrioventricular Conduction," *J. Cardiovasc. Electrophysiol*. 11(1):64-69.

Silber, E.N. (1987). "The Treatment of Ischemic Heart Disease," Chapter 40 in *Heart Disease*, 2$^{nd}$ Edition, MacMillan Publishing Co.: New York, NY, pp. 1642-1688.

Solti, F. et al. (1973). "The Haemodynamic Basis of Anginal Relief Produced by Stimulation of the Carotid Sinus Nerve," *Acta Medica Academiae Scientiarum Hungaricae* 30(1-2):61-65.

Solti, F. et al. (1975). "Baropacing of the Carotid Sinus Nerve for Treatment of 'Intractable' Hypertension," *Zeitschrift Fur Kardiologie* 64(4):368-374.

Stefanadis, C. et al. (Feb. 2000). "Non-Invasive Heat-Delivery to Arterial Stented Segments In Vivo: Effect of Heat on Intimal Hyperplasia," Abstract No. 1041-89, *Supplement of the Journal of American College of Cardiology* 35(2):14A.

Tarver, W.B. et al. (Oct. 1992). "Clinical Experience with a Helical Bipolar Stimulating Lead," *PACE* 15(10—Part II):1545-1556.

Tsakiris, A.G. et al. (Oct. 1967). "Change in Left Venticular End-Diastolic Volume-Pressure Relationship After Acute Cardiac Denervation," *Circulation*, Supplement No. Two, American Heart Associate Abstracts, XXXVI(4):II-253.

Tuckman, J. et al. (Oct. 1967). "Use of Radio Frequency Carotid Sinus Nerve Stimulators in Severe Hypertension: II," *Circulation*, Supplement No. Two, American Heart Associate Abstracts, XXXVI(4):II-253.

Yatteau, R.F. et al. (Apr. 1, 1971). "Laryngospasm Induced by a Carotid-Sinus-Nerve Stimulator," T*he New England Journ. of Med.* 284(13):709-710.

* cited by examiner

DEVICES, SYSTEMS, AND METHODS FOR IMPROVING LEFT VENTRICULAR STRUCTURE AND FUNCTION USING BAROREFLEX ACTIVATION THERAPY

CROSS-REFERENCE TO RELATED APPLICATIONS

This application claims priority to U.S. Provisional Patent Application Ser. No. 60/895,913 filed on Mar. 20, 2007, which is hereby incorporated by reference in its entirety.

BACKGROUND

Congestive heart failure (CHF) may be considered a condition in which cardiac output is not adequate to meet the metabolic needs of the body, either at rest or with exercise, usually accompanied by an increase in cardiac filling pressure and/or volume. Implicit in that physiological definition is that CHF can be caused by an abnormality in systolic function leading to a defect in expulsion of the blood (systolic HF), or by an abnormality in diastolic function leading to a defect in ventricular filling (diastolic HF).

Patients suffering from systolic heart failure (SHF) typically exhibit reduced or weakened pumping action of the heart, and is characterized by impaired ventricular contraction, most likely due to changes in the signal transduction mechanisms regulating cardiac excitation-contraction coupling. The result is a decrease in stroke volume and a compensatory rise in preload (often measured as ventricular end-diastolic pressure or pulmonary capillary wedge pressure). A common clinical measurement is the ejection fraction (EF). The ejection fraction is a calculation of how much blood is ejected out of the left ventricle (stroke volume), divided by the maximum volume remaining in the left ventricle at the end of diastole or relaxation phase. A normal ejection fraction is greater than 50%. Systolic heart failure has a decreased ejection fraction of less than 50%.

Because the ventricle is inadequately emptied, ventricular end-diastolic pressure and volumes increase. This is transmitted to the atrium. On the left side of the heart, the increased pressure is transmitted to the pulmonary vasculature, and the resultant hydrostatic pressure favors extravassation of fluid into the lung parenchyma, causing pulmonary edema. On the right side of the heart, the increased pressure is transmitted to the systemic venous circulation and systemic capillary beds, favoring extravassation of fluid into the tissues of target organs and extremities, resulting in dependent peripheral edema. Progressive worsening of heart failure can lead to cardiogenic shock, arrhythmias, electromechanical dissociation, and death.

Many SHF patients are treated with drugs, including those drugs designed for the purpose of directly stimulating cardiac tissue in order to increase contractility. However, drugs have possible undesirable side effects, and drugs do not always work for their intended purpose. There have also been a number of device therapies investigated.

Additional therapies have focused on the role that nitric oxide (NO) may play in heart failure. NO is a diffusible highly reactive gas formed by three NO synthase (NOS) isoforms: neuoronol, inducible, and endothelial. NO is produced by the vascular endothelium and serves to promote vascular homeostatis. It has been hypothesized that endothelial nitric oxide synthase (eNOS) in the left ventricle is decreased in instances of SHF, and neuronal nitric oxide synthase (nNos) and inducible nitric oxide synthase (iNOS) in the left ventricle are increased in instances of SHF. Further, cardiac β-adrenergic receptor (β-AR) signaling is impaired leading to desensitization of the myocardium to catecholamines.

Given the high incidence of SHF with left ventricular dysfunction, additional devices and methods of treatment would be desirable.

BRIEF SUMMARY

Described here are devices, systems, and methods for improving left ventricular function and structure using baroreflex activation therapy. In general the systems comprise at least one electrode and a control system in communication with the electrode, the control system including a processor and memory, wherein the memory includes software defining a stimulus regime configured to effect improvement in left ventricular function and structure. Of course, other suitable devices are also described here.

Methods for improving left ventricular function in a subject typically comprise identifying a patient in need of left ventricular function improvement and stimulating a baroreflex with a baroreflex activation device to improve left ventricular function. In some variations the baroreflex activation device is implanted proximate the baroreceptor, and in other variations, the baroreflex activation device is external. The stimulation provided by the baroreflex activation device may be any suitable stimulation. For example, it can be electrical stimulation, mechanical stimulation, thermal stimulation, chemical stimulation, or combinations thereof. In some variations the stimulation is electrical stimulation. The stimulation may be pulsed or continuous.

In some variations, the baroreflex targeted for therapy may activate baroreceptors. In some variations, the baroreflex targeted may activate mechanoreceptors. In some variations, the baroreflex targeted may activate pressoreceptors. In some variations, the baroreflex targeted is located in a vein, e.g., the inferior vena cava, the superior vena cava, the portal vein, the jugular vein, the subclavian vein, iliac vein, azygous vein, pulmonary vein, or femoral vein. In other variations, the baroreflex activation target is located in a carotid sinus, aortic arch, heart, common carotid artery, subclavian artery, pulmonary artery, femoral artery, or brachiocephalic artery.

Typically the improvement in left ventricular function and structure are confirmed. In some variations, the improvement is confirmed by a hemodynamic measurement (e.g., left ventricular pressure, peak rate of change of left ventricular pressure during isovolumic contraction, left ventricular end-diastolic pressure, mean pulmonary artery pressure, mean pulmonary artery wedge pressure, mean right atrial pressure, cardiac output, left ventricular stroke volume, cardiac index, and combinations thereof). In other variations, the improvement is confirmed by an angiographic measurement (e.g., a ventriculogram). The improvement in left ventricular function and structure may also be confirmed by echocardiography and Doppler.

The methods require identifying a patient in need of left ventricular function improvement, and such identification may be done in any suitable manner. For example, the identification may comprise identifying a patient having low ejection fraction, low cardiac output, increased end diastolic volume, ischemia, ventricular pump impairment, or combinations thereof.

In some variations, the methods further comprise the administration of one or more active agents, and any suitable active agent may be used. In some variations, the active agents are useful in treating heart failure, e.g., they are selected from the group consisting of ACE inhibitors, diuretics, vasodilators, angiotensin II receptor blockers, beta-blockers, cardiac glycosides, anticoagulants, positive inotropic drugs, and combinations thereof. In other variations, the methods further comprise implanting one or more devices for improving left ventricular function and structure.

DETAILED DESCRIPTION

Figure 1:
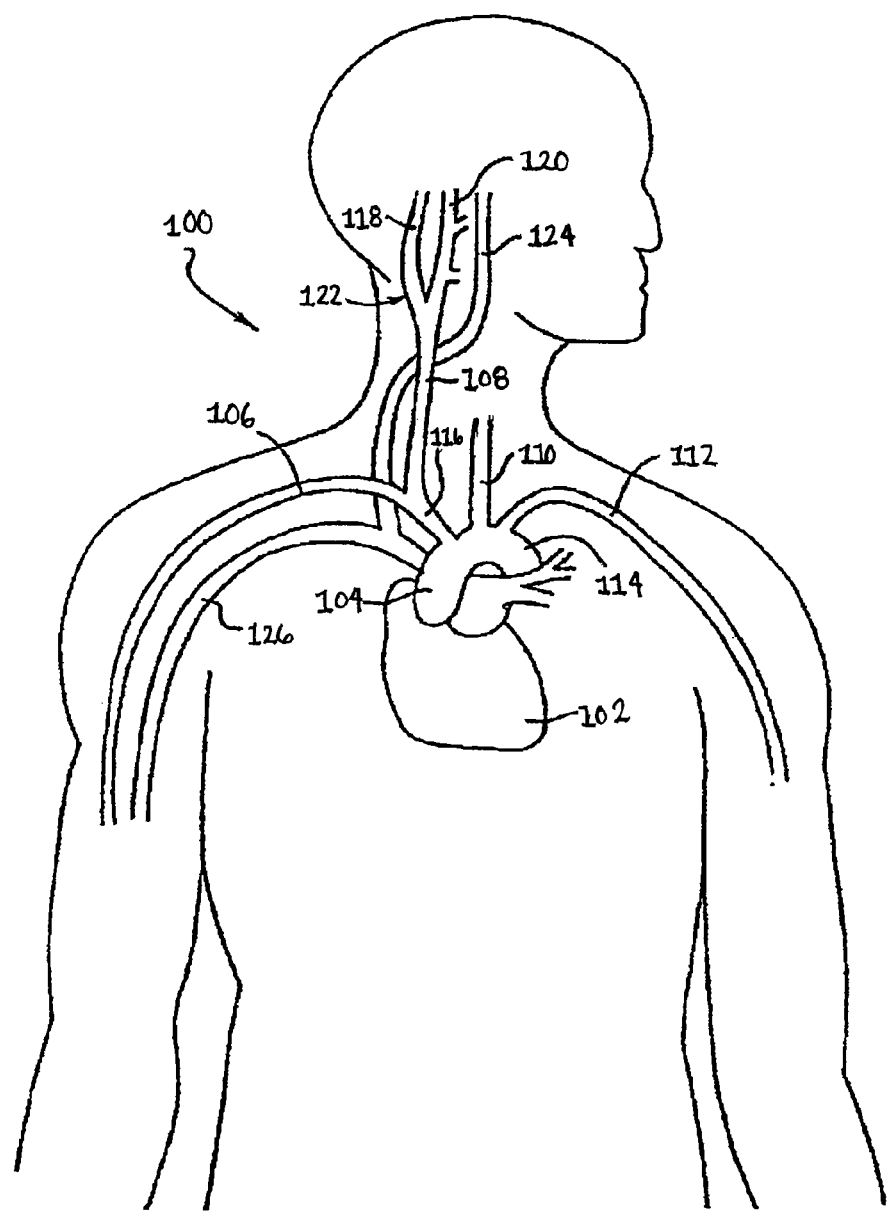
FIG. 1 is a schematic illustration of the upper torso of a human body showing the major arteries and veins and associated anatomy.

Described here are devices, systems and methods for improving left ventricular function and structure using baroreflex activation therapy. To better understand the methods, systems, and devices described here, it may be useful to explain some of the basic vascular anatomy associated with the cardiovascular system. FIG. 1 provides an illustrative depiction of the upper torso of a human body 100 showing some of the major arteries and veins of the cardiovascular system. The left ventricle of the heart 102 pumps oxygenated blood up into the aortic arch 104. The right subclavian artery 106, the right common carotid artery 108, the left common carotid artery 110, and the left subclavian artery 112, branch off the aortic arch 104 proximal of the descending thoracic aorta 114. Although relatively short, a distinct vascular segment referred to as the brachiocephalic artery 116 connects the right subclavian artery 106 and the right common carotid artery 108 to the aortic arch 104. The right carotid artery 108 bifurcates into the right external carotid artery 118 and the right internal carotid artery 120 at the right carotid sinus 122. The left carotid artery 110 similarly bifurcates into the left external carotid artery and the left internal carotid artery at the left carotid sinus.

From the aortic arch 104, oxygenated blood flows into the carotid arteries 118/120 and the subclavian arteries 106/112. From the carotid arteries 118/120, oxygenated blood circulates through the head and cerebral vasculature and oxygen depleted blood returns to the heart by way of the jugular veins, of which only the right internal jugular vein 124 is shown for sake of clarity. From the subclavian arteries 106/112, oxygenated blood circulates through the upper peripheral vasculature and oxygen depleted blood returns to the heart by way of the subclavian veins, of which only the right subclavian vein 126 is shown, also for sake of clarity. The heart 102 pumps the oxygen depleted blood through the pulmonary system where it is re-oxygenated. The re-oxygenated blood returns to the heart which pumps the re-oxygenated blood into the aortic arch as described above, and the cycle repeats.

Within the arterial walls of the aortic arch 104, common carotid arteries 108/110 (near the right carotid sinus 122 and left carotid sinus), subclavian arteries 106/112 brachiocephalic artery 116, heart, etc., there are baroreceptors. Baroreceptors are sensory nerve endings that are sensitive to stretching due to increased pressure. These receptors send signals to the brain, which in turn regulates the cardiovascular system to maintain normal blood pressure (the baroreflex), in part through activation of the sympathetic nervous system.

Stimulation of barorecpetors has previously been proposed to reduce blood pressure and the workload of the heart in the treatment of high blood pressure and angina. For example, U.S. Pat. No. 6,073,048 to Kieval et al. discloses a baroreflex modulation system and method for stimulating the baroreflex based on various cardiovascular and pulmonary parameters. Implantable devices for treating high blood pressure or hypertension by stimulating various nerves and tissue in the body are known and described, for example, in U.S. Pat. No. 3,650,277 (stimulation of carotid sinus nerve), U.S. Pat. No. 5,707,400 (stimulation of vagal nerve), and U.S. Pat. No. 6,522,926 (stimulation of baroreceptors), each of which is incorporated by reference herein. Surprisingly, it has been found that baroreflex activation therapy may be useful in improving left ventricular function in patients with systolic heart failure with left ventricular dysfunction.

Systems

Figure 2:
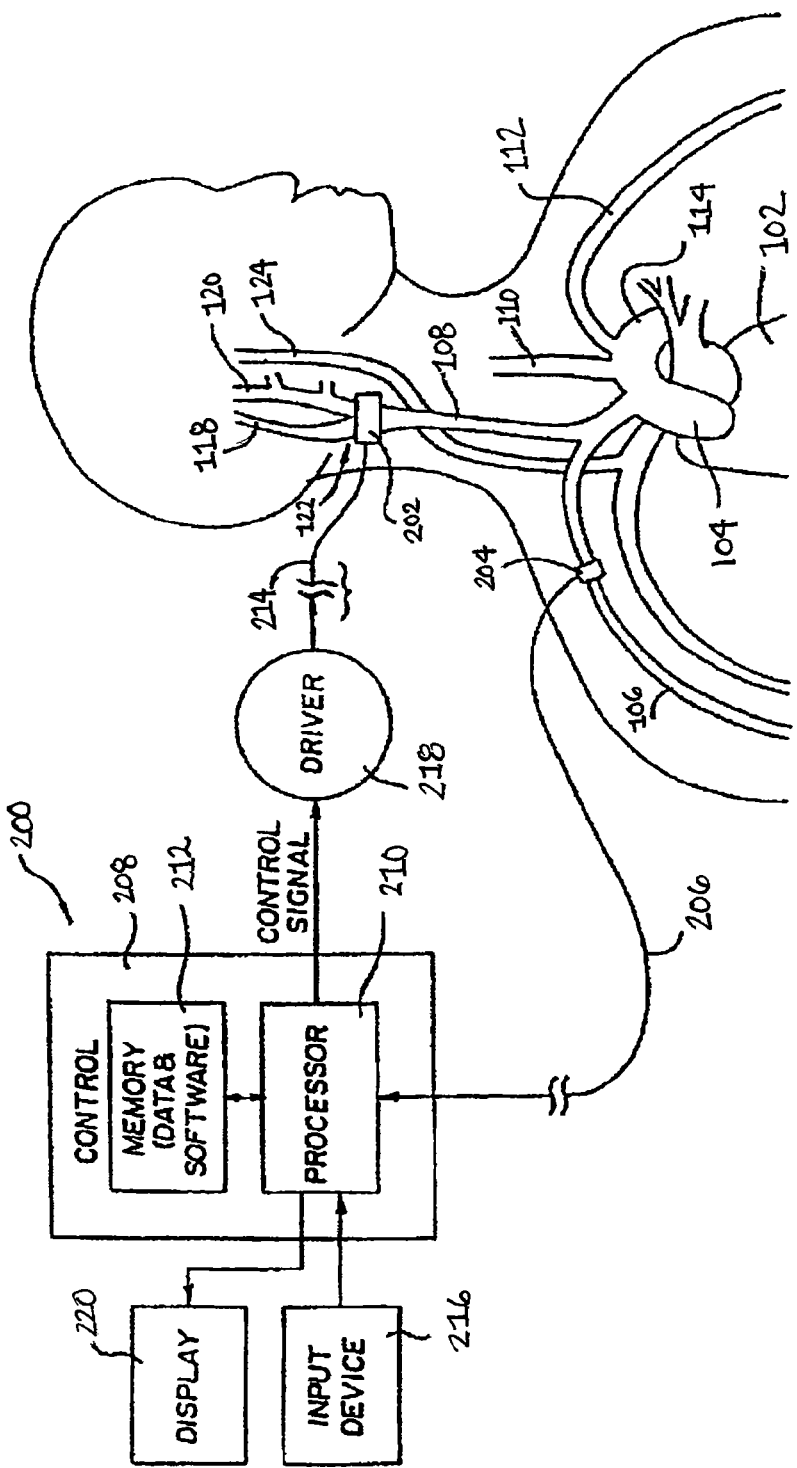
FIG. 2 provides one variation of an illustrative baroreflex activation system for use with the methods described herein.

One illustrative baroreflex activation system for use with the methods described herein is shown in FIG. 2. Shown there are control system 200, baroreflex activation device 202, and optional sensor 204. Optional sensor 204 may be used to sense and/or monitor a parameter (e.g., cardiovascular function, or more particularly, left ventricular function and/or structure), and generate a signal indicative of the parameter. The control system 200 generates a control signal as a function of the received sensor signal. The control signal activates, deactivates or otherwise modulates the baroreflex activation device 202. Typically, activation of the device 202 results in activation of the baroreflex. Alternatively, deactivation or modulation of the baroreceptor activation device 202 may cause or modify activation of the baroreflex. The baroreflex activation device 202 may comprise a wide variety of devices that can utilize mechanical, electrical, thermal, chemical, biological, or other mechanisms to activate the baroreflex. Thus, when the sensor 204 detects a parameter indicative of the need to modify the baroreflex system activity, the control system 200 generates a control signal to modulate (e.g., activate) the baroreflex activation device 202. Similarly, when the sensor 204 detects a parameter indicative of normal left ventricular function and/or structure, the control system 200 generates a control signal to modulate (e.g., deactivate) the baroreflex activation device 202.

As mentioned previously, the baroreflex activation device 202 may comprise a wide variety of devices which utilize mechanical, electrical, thermal, chemical, biological or other mechanisms to activate the baroreflex. In most instances, particularly the mechanical activation variations, the baroreflex activation device 202 indirectly activates the baroreflex by stretching or otherwise deforming the vascular wall surrounding the baroreceptors. In other variations, particularly the non-mechanical activation variations, the baroreflex activation device 202 may directly activate the baroreflex by changing the electrical, thermal or chemical environment or potential across the baroreceptors. It is also possible that changing the electrical, thermal or chemical potential across the tissue surrounding the baroreceptors may cause the surrounding tissue to stretch or otherwise deform, thus mechanically activating the baroreflex. In other variations, particularly the biological activation variations, a change in the function or sensitivity of the baroreceptors may be induced by changing the biological activity in the baroreceptors and altering their intracellular makeup and function.

The baroreflex activation device may be implanted in any suitable fashion, and in some variations, it is implanted using a minimally invasive percutaneous translumenal approach and/or a minimally invasive surgical approach, depending on whether the device 202 is disposed intravascularly, extravascularly or within a vascular wall. While depicted as implanted near the right carotid sinus in FIG. 2, it should be understood that the baroreflex activation device 202 may be positioned anywhere, such as in the heart 102, in the aortic arch 104, in the common carotid arteries 118/120 near the carotid sinus 122, in the subclavian arteries 106/112, or in the brachiocephalic artery 116. The baroreflex activation device 202 may be implanted such that the device is positioned immediately adjacent baroreceptors. Alternatively, the baroreflex activation device may be outside the body such that the device is positioned a short distance from, but proximate to baroreceptors. In some variations, the baroreflex activation device is implanted near the right carotid sinus 122 and/or the left carotid sinus (near the bifurcation of the common carotid artery) and/or the aortic arch 104, where the baroreceptors have a significant impact on the baroreflex system.

The optional sensor 204 may be operably coupled to the control system 200 by electric sensor cable or lead 206. The sensor 204 may comprise any suitable device that measures or monitors a parameter indicative of left ventricular dysfunction, and it should be understood that the sensor may be placed in any suitable location to effect a suitable measurement (e.g., within the heart). In addition, it should be understood that any number of sensors may be used, and the sensor need not be implanted, or be part of the baroreflex activation system.

By way of example, the control system 200 includes a control block 208 comprising a processor 210 and a memory 212. Control system 200 may be connected to the sensor 204 by way of sensor cable 206. Control system 200 may be connected to the baroreflex activation device 202 by way of electric control cable 214. Thus, the control system 200 may receive a sensor signal from the sensor 204 by way of sensor cable 206, and transmit a control signal to the baroreflex activation device 202 by way of control cable 214.

The memory 212 may contain data related to the sensor signal, the control signal, and/or values and commands provided by the input device 216. The memory 212 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

As mentioned previously, the baroreflex activation device 202 may activate the baroreflex mechanically, electrically, thermally, chemically, biologically or otherwise. In some instances, the control system 200 includes a driver 218 to provide the desired power mode for the baroreflex activation device 202. For example if the baroreflex activation device 202 utilizes pneumatic or hydraulic actuation, the driver 218 may comprise a pressure/vacuum source and the cable 214 may comprise fluid line(s). If the baroreflex activation device 202 utilizes electrical or thermal actuation, the driver 218 may comprise a power amplifier or the like and the cable 214 may comprise electrical lead(s). If the baroreflex activation device 202 utilizes chemical or biological actuation, the driver 218 may comprise a fluid reservoir and a pressure/vacuum source, and the cable 214 may comprise fluid line(s). In other instances, the driver 218 may not be necessary, particularly if the processor 210 generates a sufficiently strong electrical signal for low level electrical or thermal actuation of the baroreflex activation device 202.

The control system 200 may operate as a closed loop utilizing feedback from the sensor 204, or as an open loop utilizing commands received by input device 216. The open loop operation of the control system 200 preferably utilizes some feedback from the sensor 204, but may also operate without feedback. Commands received by the input device 216 may directly influence the control signal or may alter the software and related algorithms contained in memory 212. The patient and/or treating physician may provide commands to input device 216. Display 65 may be used to view the sensor signal, control signal and/or the software/data contained in memory 212.

The control signal generated by the control system 200 may be continuous, periodic, episodic or a combination thereof, as dictated by an algorithm contained in memory 212. The algorithm contained in memory 212 defines a stimulus regimen which dictates the characteristics of the control signal as a function of time, and thus dictates the stimulation of the baroreflex as a function of time. Continuous control signals include a pulse, a train of pulses, a triggered pulse and a triggered train of pulses, all of which are generated continuously. Examples of periodic control signals include control signals that have a designated start time (e.g., beginning of each minute, hour or day) and a designated duration (e.g., 1 second, 1 minute, 1 hour). Examples of episodic control signals include signals that are triggered by an episode (e.g., activation by the patient/physician, an increase in blood pressure above a certain threshold, etc.). When the systems described here are configured for electrical stimulation, suitable parameters include a frequency of about 100 Hz, about 5-7 volts, and about 400 to about 500 microsecond pulse width. Suitable stimulus regimes are described generally in U.S. patent application Ser. Nos. 11/186,140 filed on Jul. 20, 2005 and 10/818,738 filed on Apr. 5, 2004, each of which is hereby incorporated by reference in its entirety.

Devices

Figure 3:
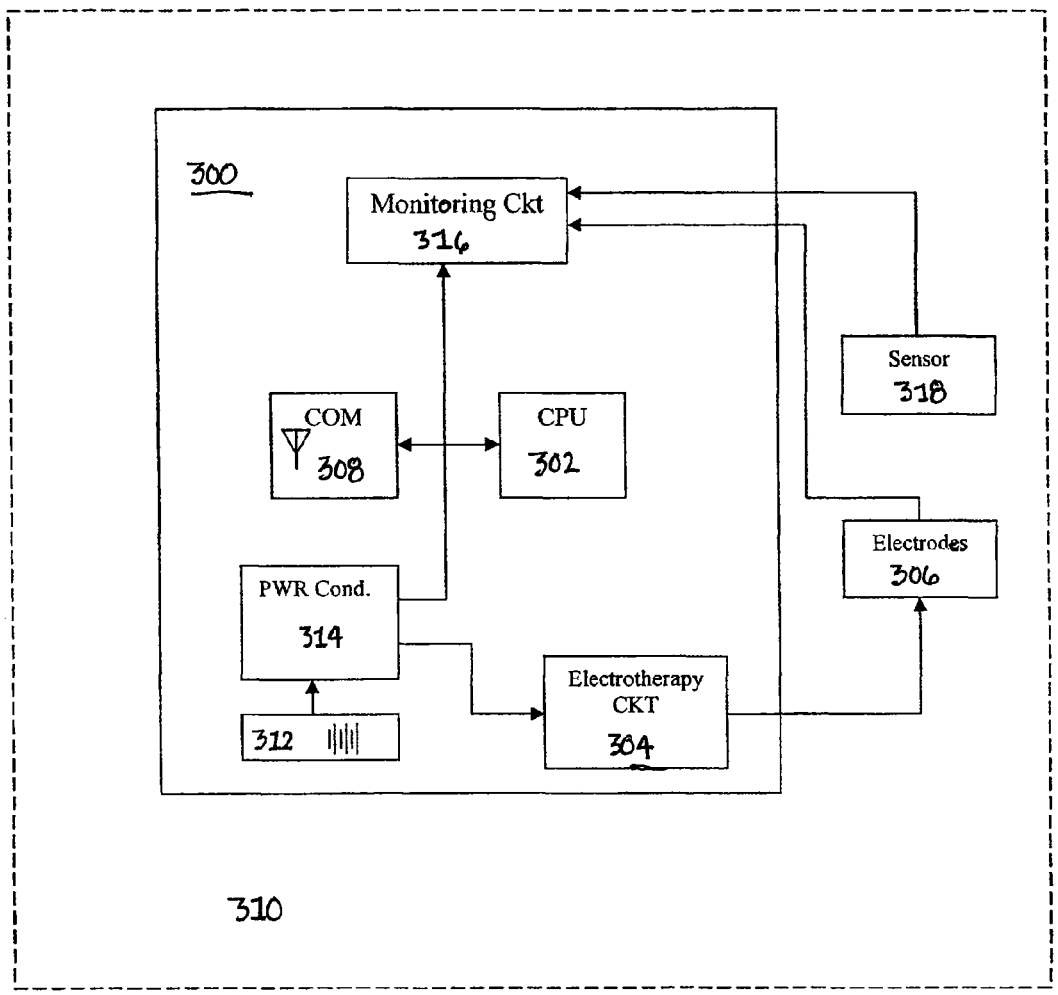
FIG. 3 is a schematic depicting illustrative components of an illustrative baroreflex activation device, for use with the methods described herein.

The devices for use with the systems and methods described herein can take on any suitable fashion, and suitable devices were described briefly above with respect to the systems. When the device is configured to improve left ventricular function and/or structure via delivery of an electrical stimulus, the device typically comprises at least one electrode. FIG. 3 provides a block diagram of an illustrative baroreflex activation device, configured to provide an electrical stimulus, and which may be used in accordance with the methods described herein. As with the device described in the system of FIG. 2, it may or may not be implanted within a subject or patient.

Shown there is device 300, which comprises a central processor unit (CPU) 302, which may include one or more microprocessors or microcontrollers, for example, configured to control the operation of the device. CPU 302 may be configured to cause the device to delivery the electrotherapy via electrotherapy circuit 304 and one or more electrodes 306. A communications circuit 308 is interfaced with CPU 302 and is used for communicating information between CPU 302 and equipment external to the patient 310, such as a device programmer (not shown), or external or remote sensors (not shown). The baroreflex activation device 300 may also comprise a power source such as a battery 312, and power conditioning circuitry 314 for converting the battery power into various power supplies suitable for powering each sub-system of the device. CPU 302 may be configured to detect at least one physiologic condition of patient 310 via patient monitoring circuitry 316 and at least one sensor 318.

Figure 4:
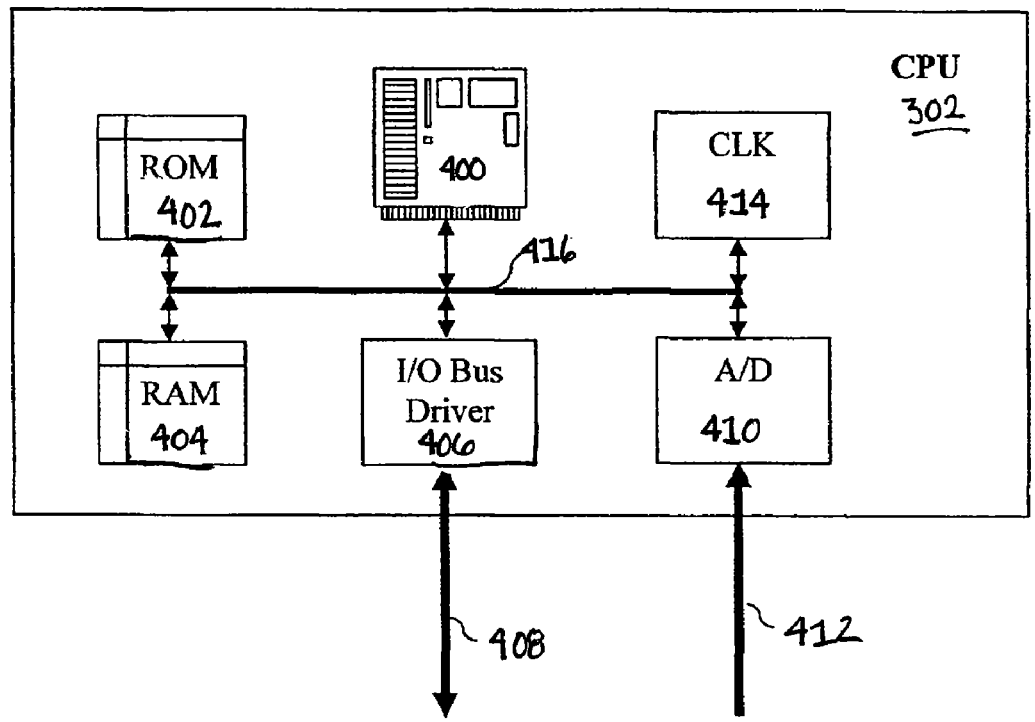
FIG. 4 depicts additional suitable features of the central processing unit (CPU) of the baroreflex activation device of FIG. 3.

FIG. 4 provides an illustrative depiction of one variation of CPU 302. In this variation, CPU 302 includes a microprocessor core 400, read-only memory (ROM) 402 for storing instructions, random access memory (RAM) 404 for use as data gathering, or scratchpad memory during operation, input/output (I/O) bus driving circuitry 406 for transmitting and receiving information via, and controlling the use of, I/O bus 408, analog-to-digital (A/D) converter 410 for converting analog signals received via analog inputs 412 into a digital format for use by microprocessor core 400, and clock 414 for providing a time base for use by microprocessor core 400. In one variation, CPU 302 has signal processing capability (such as that provided by a DSP core) to perform computations on relatively long sequences of sampled data. An internal CPU interconnect 416 provides an interface between the various CPU components, and can include conventional data exchange hardware, such as a data bus, an address bus, and control lines (not shown).

Referring again to FIG. 3, in one variation, the patient monitoring circuitry 316, or at least a portion of the signal processing circuitry of CPU 302 is situated remotely from device 300 and is communicatively coupled with device 300. Similarly, sensor 318 can be remotely situated from patient monitoring circuitry 316 or from device 300.

As with the sensors described above, sensor 318 may be any sensor suitable to help detect left ventricular dysfunction. For example, the sensor may be configured to sense or help sense low ejection fraction, low cardiac output, increased end diastolic volume, ischemia, ventricular pump impairment, or combinations thereof. Any number of sensors may be used.

Methods

Methods for improving left ventricular function and/or structure are also described here. In general, the methods comprise identifying a patient in need of left ventricular function and/or structure improvement, and stimulating a baroreflex with a baroreflex activation device to improve left ventricular function and/or structure. The stimulation may be any suitable stimulation, e.g., electrical, mechanical, thermal, chemical, or any combination of the foregoing, and the stimulation may be accomplished by any suitable device (which may or may not be implanted).

The baroreflex may be activated at any suitable location, for instance, a vein (e.g., inferior vena cava, the superior vena cava, the portal vein, the jugular vein, the subclavian vein, iliac vein, azygous vein, pulmonary vein, and femoral vein), or it may be activated in another location (e.g., carotid sinus, aortic arch, heart, common carotid artery, subclavian artery, pulmonary artery, femoral artery, or brachiocephalic artery). In some variations, stimulating a baroreflex comprises stimulating a baroreceptor of the carotid sinus.

Typically the methods described herein require the identification of a patient in need of left ventricular function improvement, and identification of such a patient may be made in any suitable fashion. For example, a patient having symptoms such as shortness of breath and/or edema, as well as, low ejection fraction, low cardiac output, increased end diastolic volume, ischemia, ventricular pump impairment, or combinations thereof may be suitable for the methods described herein. Such identification methods may employ mechanisms such as angiographic methods and/or echocardiography.

Without wishing to be bound by or to any particular theory or mechanism of action, it is thought that stimulating a baroreflex with a baroreflex activation device may help improve left ventricular function by normalizing or otherwise affecting gene expression, for example, mRNA expression of eNOS, iNOS and nNOS. Our study results show that carotid baroreflex activation therapy normalizes gene expression of NOS in the left ventricular myocardium of dogs with chronic systolic heart failure with left ventricular dysfunction. In SHF, nNOS and iNOS levels are increased. This increase may be partly responsible for the reduced responsiveness of the failing myocardium to exogenous catecholamines.

To determine the effect of long term carotid BAT on the levels of NOS, total RNA was extracted from the left ventricular myocardium of 8 BAT-treated dogs with systolic heart failure, 6 untreated dogs with systolic heart failure and 6 dogs without systolic heart failure after a 3 month period. The RNA was reverse transcribed into cDNA. Using forward and reverse primers, the cDNA specific to GAPDH and to eNOS, nNOS and iNOS was amplified by reverse transcription polymerase chain reaction. Bands of GADPH, eNOS, nNOS and iNOS were identified using ethidium bromide agarose gel electrophoresis and were quantified in densimetric units.

Figure 5:
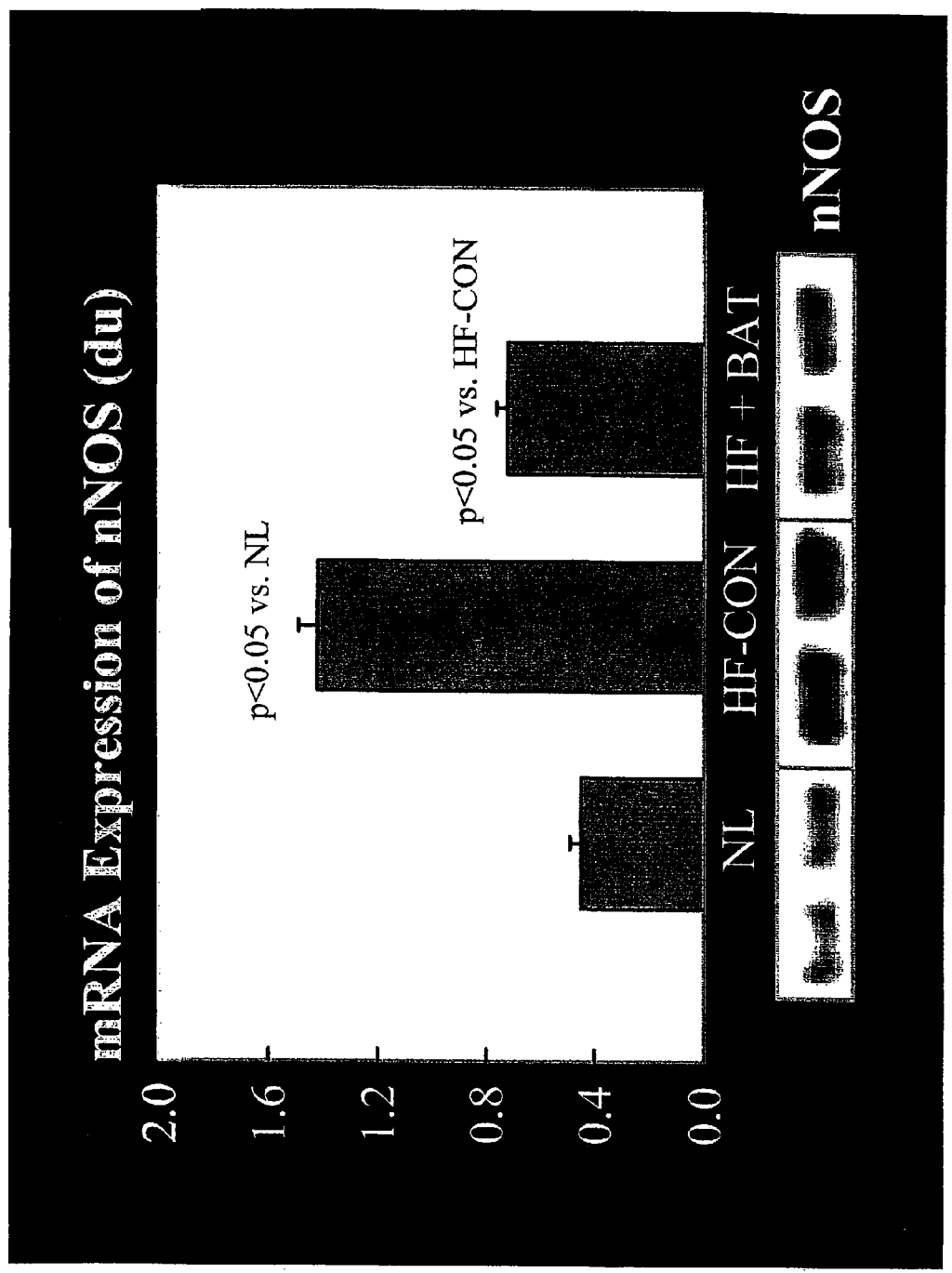
FIG. 5 provides a graphical representation of mRNA expression of nNOS.
Figure 6:
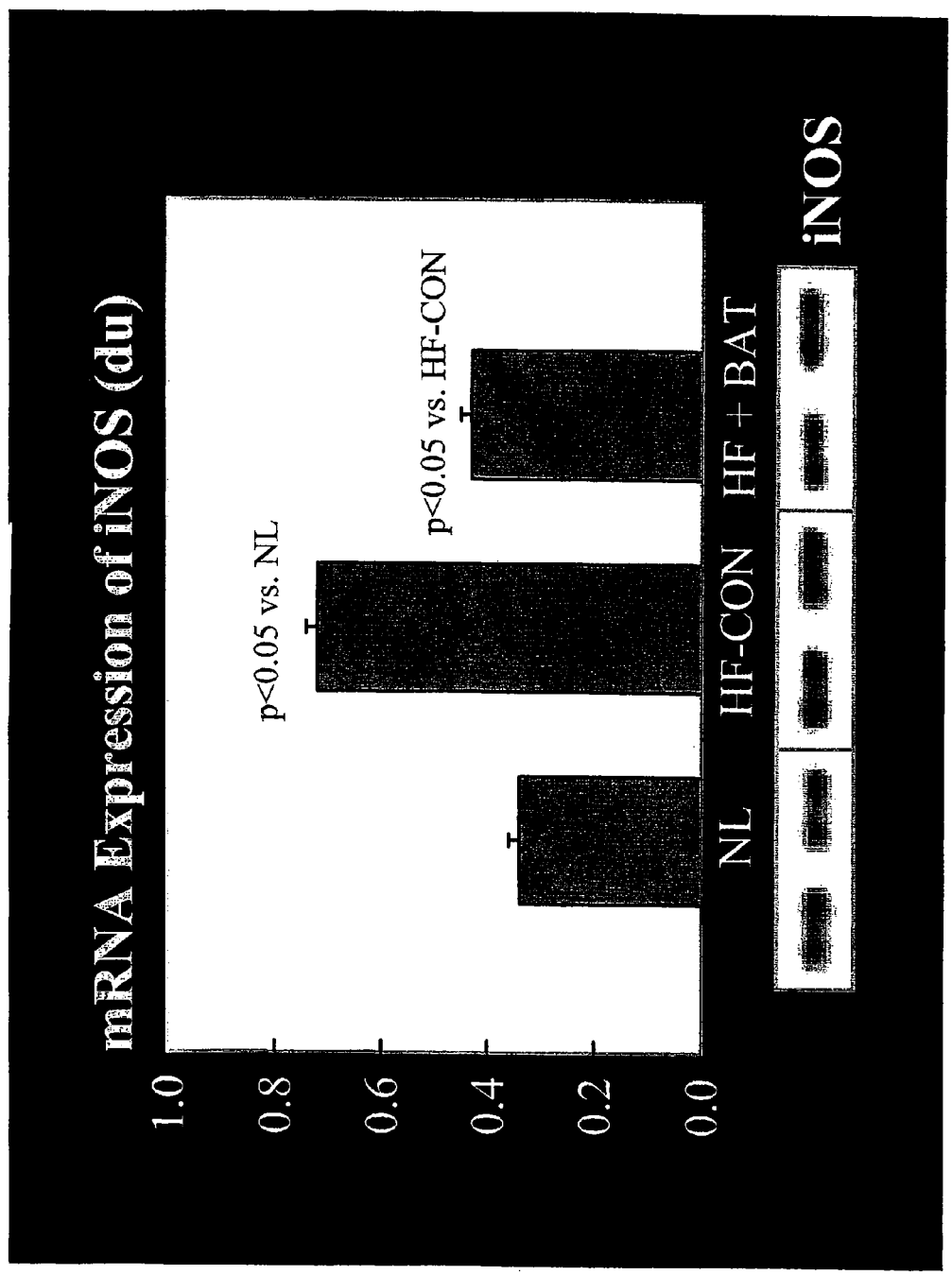
FIG. 6 provides a graphical representation of mRNA expression of iNOS.
Figure 7:
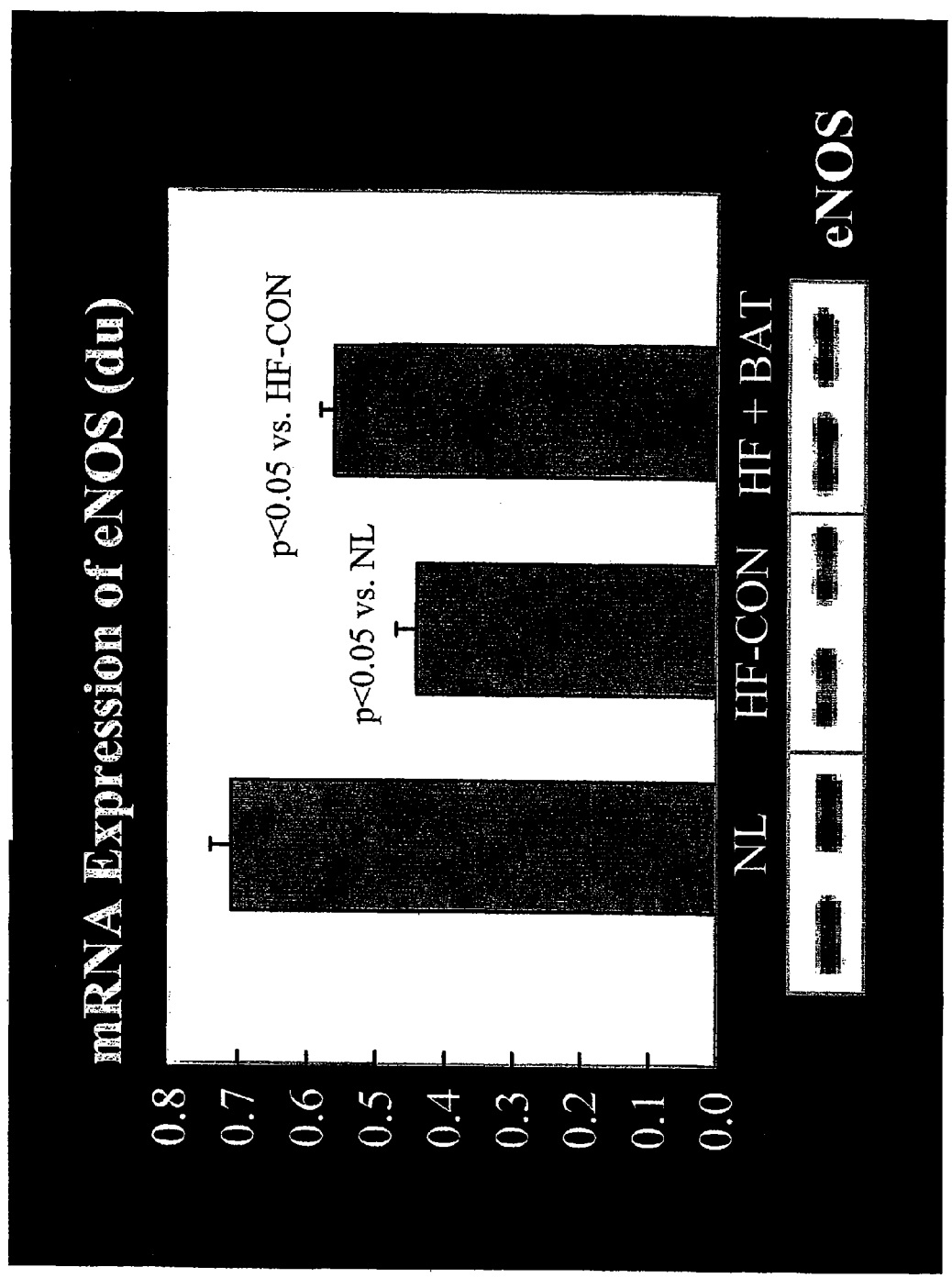
FIG. 7 provides a graphical representation of mRNA expression of eNOS.

Referring now to FIG. 5, it can be seen that mRNA expression of nNOS in untreated systolic heart failure dogs increased significantly as compared to non-heart failure dogs. The mRNA expression of nNOS was normalized in BAT treated dogs. FIG. 6 shows that the mRNA expression of iNOS increased significantly in untreated systolic heart failure dogs as compared to non-heart failure dogs. In contrast, the mRNA expression of iNOS was normalized in the BAT treated dogs with systolic heart failure. The BAT treated dogs with heart failure showed marked improvement in left ventricular function. FIG. 7 shows that the mRNA expression of eNOS decreased in untreated systolic heart failure dogs as compared to non-heart failure dogs.

In yet another embodiment, the baroreflex electrostimulation device may be used in carotid baroreflex activation therapy (BAT) to normalize gene expression, such as for example, mRNA expression of components of the β-AR signaling pathway. Our study results show that after a three month period, BAT normalized mRNA expression of β1-AR, inhibitory guanine nucleotide proteins (Gi) and β-adrenergic receptor kinase-1 (BARK-1) without affecting expression of stimulatory guanine nucleotide proteins (Gs), β2-AR, and GAPDH.

To determine the effect of long term carotid BAT, total RNA was extracted from the left ventricular myocardium of 8 BAT-treated dogs with systolic heart failure, 6 untreated dogs with heart failure and 6 dogs without heart failure after a 3 month period. mRNA expression of β1-AR, (Gi), (BARK-1) (Gs), β2-AR, and GAPDH was determined using reverse transcription polymerase chain reaction. Bands of β1-AR, (Gi), (BARK-1) (Gs), β2-AR, and GAPDH were identified and quantified in densimetric units. Compared to normal, non-heart failure dogs, mRNA expression of β1-AR decreased and mRNA expression of Gi and BARK-1 increased in untreated systolic heart failure dogs. The levels of Gs, GAPDH and β2-AR were unchanged in untreated dogs. BAT normalized the mRNA expression of β1-AR, Gi and BARK-1 without affecting the expression of Gs, GAPDH and β2-AR. This normalization of gene expression is likely to restore sensitivity to the failing myocardium to catecholamines and lead to improved left ventricular function following baroreflex activation therapy.

Without having to determine whether or not gene expression has been normalized, or otherwise affected, improvement in left ventricular function following the baroreflex activation therapy may be confirmed. For example, improvement in left ventricular function may confirmed by a hemodynamic measurement (e.g., left ventricular pressure, peak rate of change of left ventricular pressure during isovolumic contraction, left ventricular end-diastolic pressure, mean pulmonary artery pressure, mean pulmonary artery wedge pressure, mean right atrial pressure, improved ejection fraction, cardiac output, left ventricular stroke volume, cardiac index, and combinations thereof). In other variations, the improvement in left ventricular function and/or structure is confirmed by an angiographic measurement (e.g., a ventriculogram). The improvement may also be confirmed by echocardiography and Doppler.

Combination Therapies

The methods described here also contemplate combination therapies. For example, the methods described here may further comprise administering an active agent or using a supplemental device for affecting or otherwise improving left ventricular dysfunction (e.g., annuloplasty rings, and the like). The active agents may or may not be useful in treating heart failure, although in some variations, the active agents are useful in treating systolic heart failure. Illustrative systolic heart failure agents include ACE inhibitors (e.g., benazepril, captopril, enalapril, fosinopril, lisinopril, moexipril, perindopril, quinapril, ramipril, trandolapril, etc.), diuretics (bumetanide, ethacrynic acid, furosemide, amiloride, spironolactone, triamterene, chlorthalidone, hydrochlorothiazide, indapamide, metolazone, etc.), vasodilators (hydralazine, isosorbide dinitrate, nitroglycerin, etc.), angiotensin II receptor blockers (candesartan, eprosartan, irbesartan, losartan, telmisartan, valsartan, etc.), beta-blockers (bisoprolol, carvedilol, metoprolol, etc.), cardiac glycosides (digitoxin, digoxin, etc.), anticoagulants (heparin, warfarin, etc.), positive inotropic drugs (inamrinone, dobutamine, dopamine, milrinone, etc.), and combinations thereof.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

What we claimed is:

1. A method for improving left ventricular function in a patient demonstrating symptoms of systolic heart failure with left ventricular dysfunction comprising:
    identifying a patient in need of such improvement;
    implanting a baroreflex activation device on a blood vessel, the blood vessel having a baroreceptor within its wall; and
    activating a baroreflex in the patient to improve left ventricular function by electrically stimulating the baroreceptor using the baroreflex activation device.

2. The method of claim 1, wherein the stimulation is pulsed.

3. The method of claim 1, wherein the stimulation is continuous.

4. The method of claim 1, wherein the baroreceptor is located in a vein.

5. The method of claim 4, wherein the vein is selected from the group consisting of the inferior vena cava, the superior vena cava, the portal vein, the jugular vein, the subclavian vein, iliac vein, azygous vein, pulmonary vein, and femoral vein.

6. The method of claim 1, wherein the baroreceptor is located in a carotid sinus, aortic arch, heart, common carotid artery, subclavian artery, pulmonary artery, femoral artery, or brachiocephalic artery.

7. The method of claim 1, wherein improvement in left ventricular function is confirmed by a hemodynamic measurement.

8. The method of claim 7, wherein the hemodynamic measurement is selected from the group consisting of left ventricular pressure, peak rate of change of left ventricular pressure during isovolumic contraction, left ventricular end-diastolic pressure, mean pulmonary artery pressure, mean pulmonary artery wedge pressure, mean right atrial pressure, cardiac output, left ventricular stroke volume, cardiac index, and combinations thereof.

9. The method of claim 1, wherein improvement in left ventricular function is confirmed by an angiographic measurement.

10. The method of claim 9, wherein the angiographic measurement is a left ventriculogram.

11. The method of claim 1, wherein improvement in left ventricular function is confirmed by echocardiography and Doppler.

12. The method of claim 1, wherein identifying a patient in need of left ventricular function improvement comprises identifying a patient having low ejection fraction, low cardiac output, increased end diastolic volume, ischemia, ventricular pump impairment, or combinations thereof.

13. The method of claim 1, further comprising administering one or more active agents.

14. The method of claim 13, wherein the active agent is selected from the group consisting of ACE inhibitors, diuretics, vasodilators, angiotensin II receptor blockers, beta-blockers, cardiac glycosides, anticoagulants, positive inotropic drugs, and combinations thereof.

15. The method of claim 1, further comprising implanting one or more devices for improving left ventricular function.

* * * * *